United States Patent [19]

Tsuchihashi et al.

[11] Patent Number: 4,496,755

[45] Date of Patent: Jan. 29, 1985

[54] OPTICALLY ACTIVE 1-(6-METHOXY-2-NAPHTHYL)-2-(ALKOX-YCARBONYL) AMINO-1-PROPANONE, ITS DERIVATIVES AND THEIR HALO ANALOGS AND THE METHODS FOR THEIR MANUFACTURE

[75] Inventors: Genichi Tsuchihashi, Tama; Shuichi Mitamura, Sagamihara; Koji Kitajima, Yokohama; Kumi Kobayashi, Tokyo, all of Japan

[73] Assignee: Sagami Chemical Research Center, Tokyo, Japan

[21] Appl. No.: 479,768

[22] Filed: Mar. 28, 1983

[30] Foreign Application Priority Data

Mar. 31, 1982 [JP] Japan ................................ 57-051397

[51] Int. Cl.$^3$ ................. C07C 125/067; C07C 125/02
[52] U.S. Cl. .................................... 560/028; 562/444; 560/56; 564/393; 549/347; 549/373; 549/452
[58] Field of Search .................... 560/28, 56; 564/393; 549/347, 373, 452; 562/444

[56] References Cited

PUBLICATIONS

Harrison et al., J. Med. Chem., 13, 203 (1970).

*Primary Examiner*—Bernard Helfin
*Attorney, Agent, or Firm*—John A. Dhuey

[57] ABSTRACT

A manufacturing method is described for the preparation of optically active 1-(6-methoxy-2-naphthyl)-2-(alkoxycarbonyl)amino-1-propanone, its derivatives and their halo analogs. The optically active 1-(6-methoxy-2-naphthyl)-2-(alkoxycarbonyl)amino-1-propanone, its derivatives and their halo analogs are useful intermediates in the preparation of 2-(6-methoxy-2-naphthyl)propionic acid, which is useful as pharmaceutical, e.g. anti-inflammatory, analgesic and anti-pyretic agents.

10 Claims, No Drawings

OPTICALLY ACTIVE 1-(6-METHOXY-2-NAPHTHYL)-2-(ALKOXYCARBONYL) AMINO-1-PROPANONE, ITS DERIVATIVES AND THEIR HALO ANALOGS AND THE METHODS FOR THEIR MANUFACTURE

BACKGROUND OF THE INVENTION

1. Field of the Invention

The present invention relates to a process for preparing pharmaceutically useful optically active 2-(6-methoxy-2-naphthyl)propionic acid, esters and pharmaceutically acceptable salts thereof. More specifically, it is concerned with a method of producing optically active intermediates which are useful in preparing the optically active 2-(6-methoxy-2-naphthyl)propionic acid, esters and pharmaceutically acceptable salts (preferably the sodium salt) referred to above.

2. State of the Art

The conventional procedures for preparing 2-(6-methoxy-2-naphthyl)propionic acid or esters thereof include the following methods:

(1) A method comprising subjecting 2-acetyl-6-methoxynaphthalene obtained by the Friedel-Crafts reaction of 2-methoxynaphthalene with acetyl chloride to the so-called Willgerodt-Kindler reaction using sulfur and morpholine to obtain (6-methoxy-2-naphthyl)acetic acid, converting the resulting compound into a methyl ester thereof, methylating the methyl ester using sodium hydride and methyl iodide to obtain methyl 2-(6-methoxy-2-naphthyl)propionate, and hydrolyzing the resulting compound with an alkali to obtain 2-(6-methoxy-2-naphthyl)propionic acid [refer to I. T. Harrison, B. Lewis, P. Nelson, W. Rooks, A. Roszkowski, A. Tomolonis, and J. H. Fried, J. Med. Chem., 13, 203 (1970)].

(2) A method comprising oxidizing 1-(6-methoxy-2-naphthyl)propene with thallium (Tl) oxide to produce 2-(6-methoxy-2-naphthyl)propanal which is then further oxidized with chromic acid to produce 2-(6-methoxy-2-naphthyl)propionic acid [refer to Japanese Patent Publication (Unexamined) No. 48648/74].

(3) A method comprising subjecting a Grignard reagent prepared from 2-bromo-6-methoxynaphthalene and magnesium metal, and a complex prepared from α-bromopropionic acid and methyl magnesium bromide to a so-called coupling reaction to produce 2-(6-methoxy-2-naphthyl)propionic acid [refer to Japanese Patent Publication (Unexamined) No. 111018/78].

(4) A method comprising reacting a solution of formaldehyde dimethylmercaptal S-oxide in tetrahydrofuran with successively butyl lithium, 2-acetyl-6-methoxynaphthalene and acetic anhydride at a low temperature, i.e., −78° C. to −20° C., to produce 1-methylsulfinyl-1-methylthio-2-acetoxy-2-(6-methoxy-2-naphthyl)-propane, treating the resulting compound with sodium methoxide to obtain 1-methylsulfinyl-1-methylthio-2-(6-methoxy-2-naphthyl)-1-propene, and subjecting the propene compound to methanolysis using a hydrogen chloride catalyst to produce methyl 2-(6-methoxy-2-naphthyl)propionate [refer to Japanese Patent Publication (Unexamined) No. 59647/78].

(5) A method comprising preparing a 2-(6-methoxy-2-naphthyl)propionic acid ester from a 1-(substituted-naphthyl)-2-bromo-1-alkanone [refer to G. Tsuchihashi, K. Kitajima, S. Mitamura, Tetrahedron Letters, 22, 4305 (1981)].

In order to produce naproxen, 2-(6-methoxy-2-naphthyl)propionic acid or an ester thereof obtained by the above methods must be finally subjected to optical resolution. [Refer, for example, to Japanese Patent Publication No. 14097/81.] However, such optical resolution is not advantageous from the economical standpoint since one-half of the dl pairs, i.e., (R)-2-(6-methoxy-2-naphthyl)propionic acid, is unnecessary and also complicated racemization steps are required to reuse the (R)-form. In addition, a very expensive reagent such as cinchonidine must be used for optical resolution. As a result of extensive studies to overcome such disadvantages accompanied with the optical resolution, the present inventors found the compounds of this invention represented by the formula (XI) above which can be converted into naproxen without using optical resolution.

SUMMARY OF THE INVENTION

The present invention relates to a manufacturing method for preparing novel optically active 1-(6-methoxy-2-naphthyl)-2-(alkoxycarbonyl)amino-1-propanone, its derivatives and their halo analogs represented by the formula

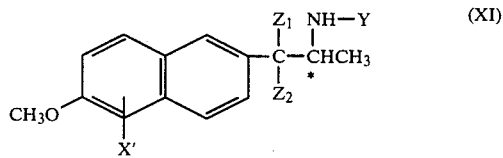

wherein X' is hydrogen or a halogen atom at the 5 or 7 position on the naphthyl moiety; $Z_1$ and $Z_2$ together with its two bonds is an oxo group or $Z_1$ and $Z_2$ are $OR^1$ groups wherein $R^1$ represents a lower alkyl group or both $R^1$s may form, when taken together an alkylene group with 2 to 6 carbon atoms; Y is —COOR (wherein R is a substituted or unsubstituted lower alkyl group) or hydrogen; $Z_1$ and $Z_2$ are $OR^1$ groups when Y is hydrogen; the asterisk mark indicates an asymmetric carbon atom.

The optically active 1-(6-methoxy-2-naphthyl)-2-(alkoxycarbonyl)amino-1-propanone, its derivatives and their halo analogs are useful intermediates in the preparation of 2-(6-methoxy-2-naphthyl)propionic acid, esters and pharmaceutically acceptable salts thereof, which are useful as pharmaceutical, e.g., anti-inflammatory, analgesic and anti-pyretic agents.

DETAILED DESCRIPTION OF THE INVENTION

The present invention relates to a manufacturing method for preparing optically active 1-(6-methoxy-2-naphthyl)-2-(alkoxycarbonyl)amino-1-propanone, its derivatives and their halo analogs represented by the formula

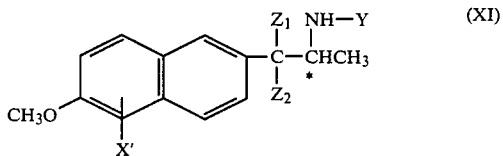

wherein X' is hydrogen or a halogen atom at the 5 or 7 position on the naphthyl moiety; $Z_1$ and $Z_2$ together with its two bonds is an oxo group or $Z_1$ and $Z_2$ are $OR^1$ groups wherein $R^1$ represents a lower alkyl group or both $R^1$s may form, when taken together an alkylene group with 2 to 6 carbon atoms; Y is —COOR (wherein R is a substituted or unsubstituted lower alkyl group) or hydrogen; $Z_1$ and $Z_2$ are $OR^1$ groups when Y is hydrogen; the asterisk mark indicates an asymmetric carbon atom.

In the present application, the term "halogen" denotes bromine, chlorine, fluorine and iodine, with bromine and chlorine being presently preferred; the term "lower alkyl group" denotes linear or branched alkyl group having 1–4 carbon atoms such as methyl, ethyl, n-propyl, isopropyl, n-butyl, isobutyl, t-butyl and it can be substituted with one or more non-interfering substituents, such as hydroxy or hydroxy derivatives; alkoxy such as methoxy, ethoxy, propoxy, butoxy and the like; acyloxy, such as acetoxy, propionoxy, butyroxy and the like; nitro groups; alkylamino groups such as dimethylamino and the like; halogens, such as fluorine, chlorine, iodine or bromine; carbonyl derivatives such as enol ethers and ketals and the like. The term "lower alkoxy group" denotes linear or branched alkoxy group having 1–4 carbon atoms such as methoxy, ethoxy, n-propoxy, iso-propoxy, n-butoxy, iso-butoxy or t-butoxy. Examples of alkylene groups of 2–6 carbon atoms are ethylene, trimethylene, butylene, pentylene, 2,2-dimethylpropylene and hexylene etc.

The compound represented by the formula

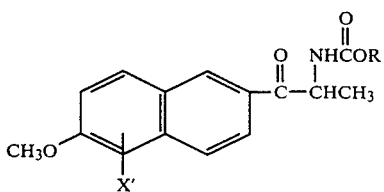

(I)

wherein X' and R are as defined above, can be prepared by reacting organo metallic compounds represented by the formula

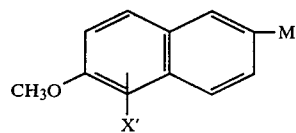

(VI)

wherein X' is as defined above; M represents MgX wherein X is a halogen atom or Li, with amides represented by the formula

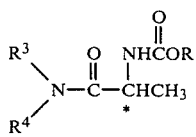

(VII)

wherein R is as defined above, $R^3$ represents a lower alkyl group, $R^4$ represents a lower alkyl group or a lower alkoxy group. The asterisk mark indicates an asymmetric carbon atom.

Reaction Scheme 1

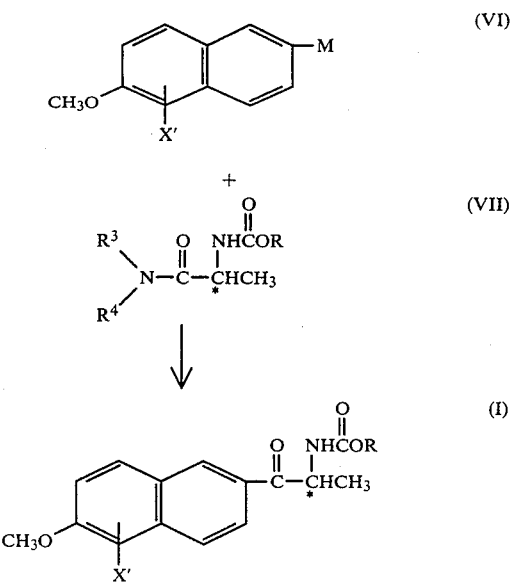

wherein X' and R are as defined above, $R^3$ represents a lower alkyl group, $R^4$ represents a lower alkyl group or a lower alkoxy group and M represents MgX (wherein X is a halogen atom) or Li.

The above reaction can be generally conducted by reacting the amide (VII) and at least 2 mol equivalents of the organometallic compound (VI), preferably in an inert solvent, at a temperature of from $-100°$ C. to room temperature, preferably $-78°$ C. to $0°$ C. Also, the reaction is preferably conducted in an inert atmosphere such as nitrogen gas or argon gas to minimize side reactions. Examples of solvents which can be preferably used are ethers such as diethyl ether, dioxane, 1,2-dimethoxyethane or tetrahydrofuran. Further, mixtures of the above ether compounds and other solvents which do not take part in the reaction, such as hexane, pentane, cyclohexane, benzene, toluene and the like, can be used.

Alternatively, the above reaction can be conducted by first reacting the amide (VII) with one mol equivalent of an alkyl lithium, an aryl lithium wherein aryl can be a monocyclic arylgroup, such as phenyl, xylyl, tolyl and the like or a condensed aryl group such as naphthyl, indenyl, anthryl, phenanthryl, d-10-camphoryl and the like, a Grignard reagent or an alkali metal hydride and then reacting with one mol equivalent of the organometallic compound (VI). Examples of alkyl lithium, aryl lithium, Grignard reagents and alkali metal hydrides which are preferred from the economical standpoint are n-, iso-, or t-butyl lithium, phenyl lithium, a methyl magnesium halide and sodium hydride, respectively.

The amides (VII) used as starting materials in the above reaction can be easily prepared from L-alanine (VIII) in accordance with the procedure shown in Reaction Scheme 2:

Reaction Scheme 2

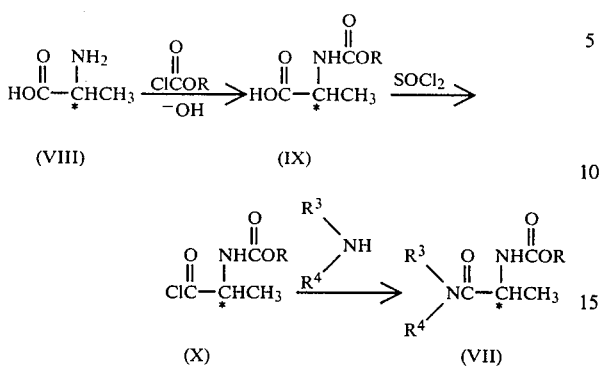

(VIII)   (IX)   (VII)

(X)

wherein R, $R^3$ and $R^4$ are as defined earlier.

Another starting compound, the organometallic compound (VI), can be prepared from 2-bromo-6-methoxynaphthalene. [Refer to Japanese Patent Publication No. 41587/79; G. Eglinton et al., J. Am. Chem. Soc., 78, 2331 (1956)] or other methods.

Compound (I) of this invention can be converted into an optically active 2-(6-methoxy-2-naphthyl)propionic ester or its halo analogs represented by the formula (IV) as shown in Scheme 3 by converting the compound (I) of this invention into a corresponding acetal (II) in a conventional manner by means of an alkanol such as methanol, ethanol, butanol, pentanol, hexanol, heptanol, octanol, and the branched chain isomers thereof or a dihydric alcohol such as ethylene glycol, trimethylene glycol, 1,3-butanediol, 1,4-butanediol, 1,4-pentanediol, 1,5-pentanediol, 2,2-dimethyl-1,3-propanediol (neopentyl glycol), 1,5-hexanediol, 1,6-hexanediol, 2,5-hexanediol and the like in the presence of an acid and of an orthoester at a temperature of from room temperature to the reflux temperature of the reaction medium, cleaving the protective group

(ROC—)

for the amino group with a base to produce an α-aminoacetal (III), reacting the resulting aminoacetal (III) with an N-nitrosolating agent such as sodium nitrite and acid preferably acetic, propionic or butyric acid and simultaneously or sequentially treating the reaction mixture with water or an aqueous solvent and, if desired, heating the reaction mixture to yield the compounds represented by the formula (IV). The compounds represented by the formula (IV) can be converted into optically active 2-(6-methoxy-2-naphthyl)-propionic acid or its halo analogs represented by the formula (V) by hydrolysis under an acidic condition without lowering the optical purity. The halogen atom at 5 or 7 position in the compounds of Formula (I)–(V) can be removed at any stages of the process by reacting the compound with a reducing agent, or as a last step in the process to yield optically active 2-(6-methoxy-2-naphthyl)propionic acid. If desired, the resulting 2-(6-methoxy-2-naphthyl) propionic acid can be further converted into its pharmaceutically acceptable salts, such as the sodium salt.

Reaction Scheme 3

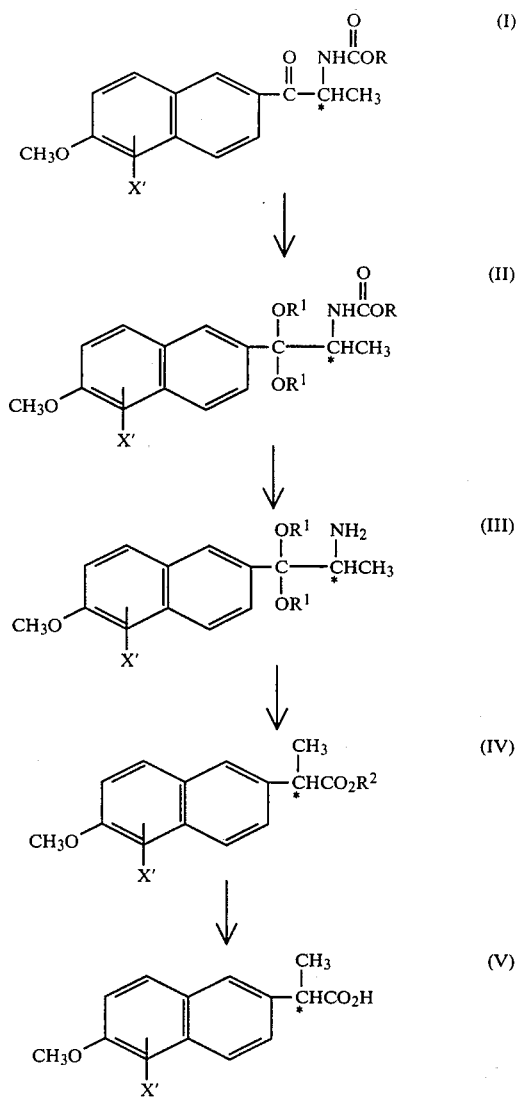

wherein X' and R are as defined earlier, $R^1$ represents a lower alkyl group, $R^2$ represents a lower alkyl group or a lower hydroxy alkyl group, and two $R^1$s may form, when taken together, an alkylene group with 2 to 6 carbon atoms.

The 2-(6-methoxy-2-naphthyl)propionic acid (i.e., the compound of formula V in which X' is hydrogen) represented by the formula (V) above, having (S) configuration with respect to the asymmetric carbon atom, is known as a pharmaceutical agent having excellent anti-inflammatory, analgesic and antipyretic activities as disclosed in U.S. Pat. No. 3,904,682, namely, anti-inflammatory agent known as naproxen.

Thus, the compounds of this invention represented by the formula (I), (II) and (III) above are very useful as precursors for the production of pharmaceutical agents such as naproxen.

The present invention is further illustrated by the embodiments described in the following examples. While the invention is described with reference to those specific embodiments, it is understood that various changes and modifications can be made, and equivalents substituted, by those skilled in the art without departing from the spirit and scope of the invention. All such modifications, changes and substitutions are intended to be within the scope of the claims appended hereto.

PREPARATION 1

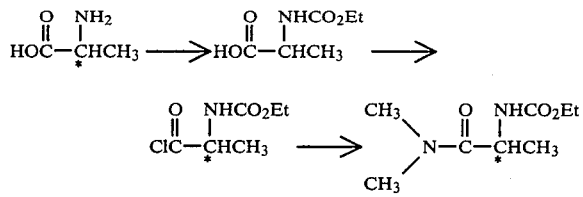

L-N-ethoxycarbonylalanine was prepared from L-alanine according to the procedure described in the literature [T. F. Buckley III, H. Rapoport, J. Am. Chem. Soc., 103, 6157 (1981)]. 5.11 g (3.17 mmols) of L-N-ethoxycarbonylalanine was dissolved in 10 ml of anhydrous methylene chloride and the solution was cooled to −10° C. 5.4 ml (74 mmols) of thionyl chloride was added thereto, and the mixture was stirred for 2 hours while gradually elevating the temperature to room temperature. THe reaction mixture was concentrated under reduced pressure to obtain 5.70 g of a crude product of 2-(ethoxycarbonylamino)propionyl chloride as a pale yellow oily substance.

NMR (CDCl$_3$): δ1.27 (3H, t, J=7 Hz), 1.54 (3H, d, J=7 Hz), 4.13 (2H, q, J=7 Hz), 4.2–4.8 (1H, m), 5.4–6.0 (broad d).

2.00 (11.0 mmols) of the crude product of 2-(ethoxycarbonylamino)propionyl chloride obtained above was dissolved in 15 ml of anhydrous diethyl ether, followed by stirring under ice-cooling. After 1.6 g (35 mmols) of dimethylamine gas was bubbled into the solution for 15 minutes, 30 ml of water was added to the mixture and the mixture was extracted with ethyl acetate (30 ml×3). The extract was dried over anhydrous magnesium sulfate and concentrated under reduced pressure to obtain 1.875 g of a crude product of (−)-N,N-dimethyl-2-(ethoxycarbonylamino)propionamide.

The product was distilled under reduced pressure to obtain 1.392 g of a pure product as a pale yellow oily substance. Yield, 67%.

Boiling point: 110°–114° C./2 Torr.

[α]$_D^{21}$ −32.1° (c=1.050, methanol).

IR (neat): 3300, 1710, 1645, 1490, 1240, 1060 cm$^{-1}$.

NMR (CDCl$_3$): δ1.22 (3H, t, J=7 Hz), 1.32 (3H, d, J=6 Hz), 2.95 (3H, s), 3.06 (3H, s), 4.08 (2H, q, J=7 Hz), 4.4–4.9 (1H, m), 5.6–6.1 (1H, broad s).

PREPARATION 2

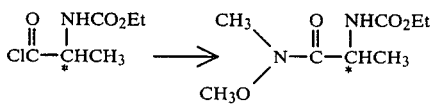

In the same manner as described in Preparation 1, 5.20 g (29.0 mmols) of 2-(ethoxycarbonylamino)propionyl chloride was prepared. This compound was then dissolved in 100 ml of anhydrous methylene chloride, and 3.70 g (37.9 mmols) of O,N-dimethylhydroxyamine hydrochloride was added thereto, followed by stirring at room temperature under argon atmosphere. 5.9 ml (5.8 g, 72 mmols) of pyridine was added to the mixture and, after stirring at room temperature for 1 hour, 200 ml of a saturated aqueous sodium chloride solution was added to the mixture. The mixture was extracted with methylene chloride (150 ml×3), and the extract was washed with 100 ml of a saturated aqueous sodium chloride solution, dried over anhydrous magnesium sulfate and concentrated under reduced pressure to obtain 6.00 g of a crude product of (−)-N-methoxy-N-methyl-2-(ethoxycarbonylamino)propionamide as a colorless oily substance. The product thus obtained was distilled under reduced pressure to obtain 4.17 g of a pure product. Yield, 71%.

Boiling Point: 100° C./0.5 Torr.

[α]$_D^{22}$ −27.9° (c=1.029, methanol).

IR (neat): 3320, 1720, 1660, 1520, 1245, 1065 cm$^{-1}$.

NMR (CDCl$_3$): δ1.23 (3H, t, J=7 Hz), 1.32 (3H, d, J=6 Hz), 3.19 (3H, s), 3.76 (3H, s), 4.09 (2H, q, J=7 Hz), 4.4–4.9 (1H, m), 5.3–5.8 (1H, broad s).

PREPARATION 3

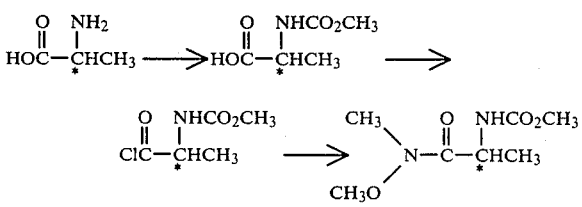

L-N-methoxycarbonylalanine was prepared from L-alanine according to the procedure described in literature [T. F. Buckley III, H. Rapoport, J. Am. Chem. Soc., 103, 6157 (1981)]. 1.87 g (12.7 mmols) of L-N-methoxycarbonylalanine was dissolved in 5 ml of anhydrous methylene chloride and the solution was cooled to −10° C., followed by stirring. 2.0 ml (28 mmols) of thionyl chloride was added thereto, and the temperature of the mixture was elevated to room temperature over a period of 2 hours. After stirring for an additional one hour at room temperature, the mixture was concentrated under reduced pressure to obtain a crude product of 2-(methoxycarbonylamino)propionyl chloride as pale yellow crystals.

NMR (CDCl$_3$): δ1.53 (3H, d, J=7 Hz), 3.72 (3H, s), 4.2–4.8 (1H, m), 4.8–5.6 (1H, broad s).

The whole amount of the crude product of 2-(methoxycarbonylamino)propionyl chloride thus obtained was dissolved in 30 ml of anhydrous methylene chloride and 1.43 g (14.6 mmol) of O,N-dimethylhydroxyamine hydrochloride was added to the solution, followed by stirring at room temperature under argon atmosphere. 2.4 ml (29 mmols) of pyridine was added dropwise to the mixture, followed by stirring at room temperature for 4 hours. 50 ml of a saturated aqueous sodium chloride solution was added to the mixture which was then extracted with ethyl acetate (30 ml×3). The extract was washed with 30 ml of a saturated aqueous sodium chloride solution, dried over anhydrous magnesium sulfate and concentrated under reduced pressure. The residue was purified by column chromatography (silica gel, ethyl acetate-hexane) to obtain 1.318 g of (−)-N-methoxy-N-methyl-2-(methoxycarbonylamino)propionamide as colorless crystals.

Melting point: 73°–74° C.

[α]$_D^{24}$ −36.7° (c=1.096, methanol).

IR (KBr): 3325, 1721, 1647, 1534, 1294, 1255, 1072, 980 cm$^{-1}$.

NMR (CDCl₃): δ1.33 (3H, d, J=7 Hz), 3.18 (3H, s), 3.65 (3H, s), 3.75 (3H, s), 4.5–4.9 (1H, m), 5.2–5.7 (1H, broad s).

Elementary Analysis: Calcd for $C_7H_{14}O_4N_2$: C, 44.20; H, 7.42; N, 14.73%; Found: C, 44.21; H, 7.67; N, 14.63%

PREPARATION 4

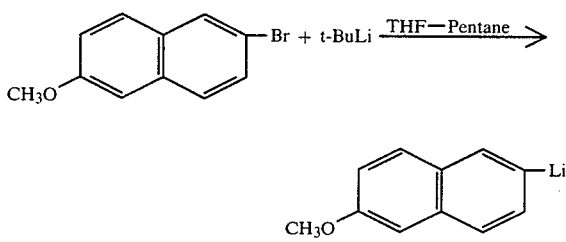

2-Bromo-6-methoxynaphthalene (10.0 mmols) was dissolved in 30 ml of anhydrous tetrahydrofuran (THF) and the solution was stirred at −78° C. under argon atmosphere. 20 ml (20 mmols) of a 1.0M pentane solution of t-butyl lithium was added dropwise to the solution over a period of 5 minutes and, after stirring at that temperature for 1.5 hours, the temperature of the mixture was elevated to −20° to −15° C. to prepare a 0.2M solution of 2-lithio-6-methoxynaphthalene. The resulting solution was used for the reaction in Examples 1 and 2.

PREPARATION 5

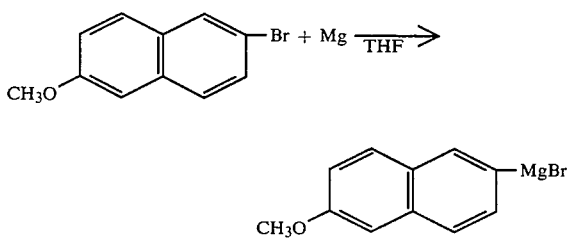

2.5 g of anhydrous tetrahydrofuran (THF) was added to 241 mg (9.9 mg-atom) of magnesium metal, and the mixture was stirred at 70° C. under argon atmosphere. An anhydrous tetrahydrofuran solution (17.5 ml) of 2.13 g (9.00 mmols) of 2-bromo-6-methoxynaphthalene was added dropwise thereto over a period of 1 hour and the mixture was stirred at the same temperature for 2 hours to prepare 0.45M tetrahydrofuran solution of 6-methoxy-2-naphthyl magnesium bromide. The resulting solution was used for the reactions in Examples 3 and 4.

EXAMPLE 1

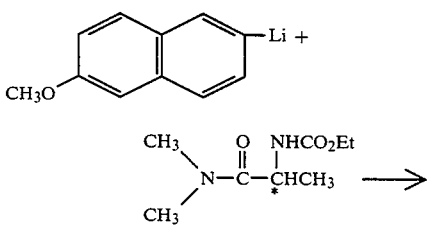

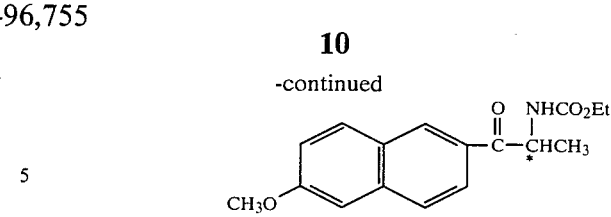

188 mg (1.00 mmol) of (−)-N,N-dimethyl-2-(ethoxycarbonylamino)propionamide was dissolved in 2 ml of anhydrous tetrahydrofuran and the solution was stirred at −78° C. under argon atmosphere. 10 ml of the 0.2M solution of 2-lithio-6-methoxynaphthalene (2.0 mmols) obtained by the reaction in Preparation 4 was added dropwise thereto over a period of 5 minutes. The mixture was stirred at that temperature for 2 hours and the temperature was then elevated gradually to room temperature. The reaction mixture was again cooled with ice and, after adding 10 ml of a 1M aqueous phosphoric acid solution, extracted with diethyl ether (20 ml×3). The extract was dried over anhydrous magnesium sulfate and concentrated under reduced pressure. The residue was separated by column chromatography [silica gel, benzene-ethyl acetate (20:1)] to obtain 190 mg of (+)-1-(6-methoxy-2-naphthyl)-2-(ethoxycarbonyl)amino-1-propanone as colorless crystals. Yield, 63%.

Melting point: 96°–97° C.

$[\alpha]_D^{22}$ +35.0° (c=1.083, methanol).

IR (KBr): 3420, 1717, 1689, 1625, 1525, 1488, 1265, 1250, 1176, 1077, 1022, 866 cm⁻¹.

NMR (CDCl₃): δ1.24 (3H, t, J=7 Hz), 1.47 (3H, d, J=7 Hz), 3.87 (3H, s), 4.13 (2H, q, J=7 Hz), 5.45 (1H, diffused dq, J=7 and 8 Hz), 5.93 (1H, diffused d, J=8 Hz), 6.9–7.3 (2H, m), 7.5–8.1 (3H, m), 8.3–8.5 (1H, broad s).

Elementary Analysis: Calcd for $C_{17}H_{19}O_4N$: C, 67.76; H, 6.35; N, 4.65%; Found: C, 67.67; H, 6.52; N, 4.55%

EXAMPLE 2

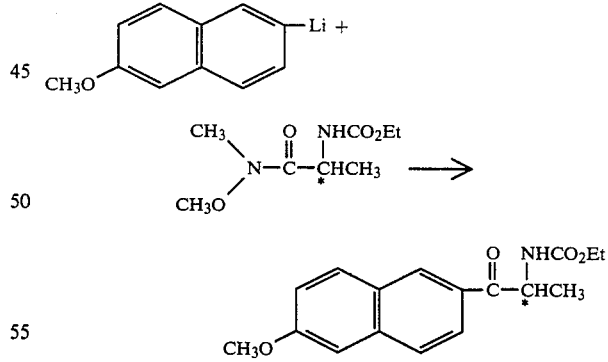

In the same manner as described in Example 1, 216 mg of (+)-1-(6-methoxy-2-naphthyl)-2-(ethoxycarbonyl)amino-1-propanone was prepared from 204 mg (1.00 mmol) of (−)-N-methoxy-N-methyl-2-(ethoxycarbonylamino)propionamide and 10 ml (2.0 mmols) of the 0.2M solution of 2-lithio-6-methoxynaphthalene prepared in Preparation 4. Yield, 72%. $[\alpha]_D^{21}$ +34.5° (c=1.014, methanol)

The product showed NMR spectrum substantially consistent with that of the product obtained in Example 1.

EXAMPLE 3

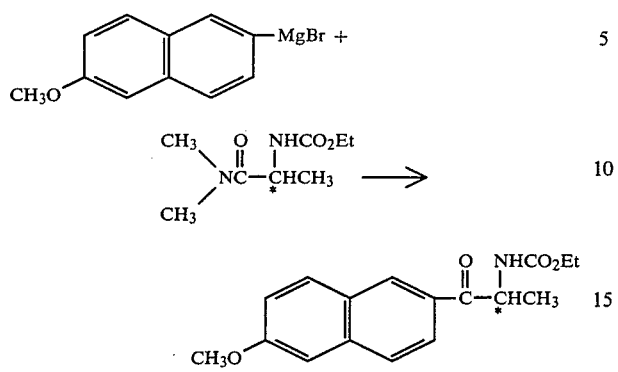

188 mg (1.0 mmol) of (−)-N,N-dimethyl-2-(ethoxycarbonaylamino)propionamide was dissolved in 3 ml of anhydrous tetrahydrofuran and the solution was stirred under argon atmosphere at −78° C. 4.4 ml of 0.45M (2.0 mmols) tetrahydrofuran solution of 6-methoxy-2-naphthyl magnesium bromide prepared by the reaction described in Preparation 5 was added dropwise to the solution and, after stirring at that temperature for 2 hours, the temperature of the mixture was elevated gradually to room temperature. The reaction mixture was cooled with ice and, after adding 20 ml of a 1M aqueous phosphoric acid solution, the mixture was extracted with methylene chloride (5 ml×3). The extract was dried over anhydrous magnesium sulfate, concentrated under reduced pressure, and the residue was separated by column chromatography [silica gel, benzene-ethyl acetate (20:1)] to obtain 131 mg of (+)-1-(6-methoxy-2-naphthyl)-2-(ethoxycarbonyl)amino-1-propanone. Yield, 44%.

$[\alpha]_D^{24}$ +32.1° (c=0.731, CH₃OH).

The product showed NMR spectrum substantially consistent with that of the product obtained by the reaction described in Example 1.

EXAMPLE 4

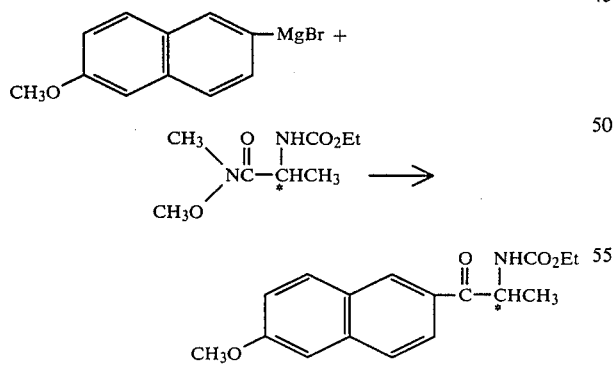

In the same manner as described in Example 3, 190 mg of (+)-1-(6-methoxy-2-naphthyl)-2-(ethoxycarbonyl)amino 1-propanone was prepared from 204 mg (1.00 mmol) of (−)-N-methoxy-N-methyl-2-(ethoxycarbonylamino)propionamide and 4.4 ml (2.0 mmols) of the 0.45M tetrahydrofuran solution of 6-methoxy-2-naphthyl magnesium bromide prepared by the reaction described in Preparation 5.

$[\alpha]_D^{24}$ +33.4° (c=1.104, methanol).

The product showed NMR spectrum substantially consistent with that of the product obtained in Example 1.

EXAMPLE 5

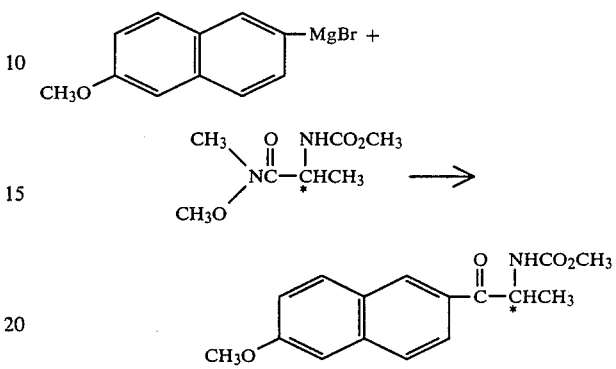

1.010 g (5.30 mmols) of (−)-N-methoxy-N-methyl-2-(methoxycarbonylamino)propionamide was dissolved in 15 ml of anhydrous tetrahydrofuran and the solution was stirred at −78° C. under argon atmosphere. 18 ml (13 mmols) of a 0.70M tetrahydrofuran solution of 6-methoxy-2-naphthyl magnesium bromide prepared by the reaction as described in Preparation 5 as added dropwise to the solution. The temperature of the mixture was allowed to raise to room temperature over a period of 3 hours and, after stirring for an additional one hour at room temperature, 60 ml of a 1M aqueous phosphoric acid solution was added to the mixture. The mixture was extracted with methylene chloride (30 ml×3), and the extract was dried over anhydrous magnesium sulfate and concentrated under reduced pressure. The residue was separated by column chromatography [silica gel, hexane-ethyl acetate (2:1)] to obtain 1.370 g of (+)-1-(6-methoxy-2-naphthyl)-2-(methoxycarbonyl)amino-1-propananone as colorless crystals. Yield, 90%.

Melting point: 107°–108° C.

$[\alpha]_D^{25}$ +26.4° (c=0.947, CH₃OH)

IR (KBr): 3350, 1686, 1628, 1540, 1278, 1181, 1071 cm⁻¹.

NMR (CDCl₃): δ1.47 (3H, d, J=7 Hz), 3.69 (3lH, s), 3.91 (3H, s), 5.43·(1H, diffused dq, J=7 and 8 Hz), 5.8 (1H, diffused d, J=8 Hz), 7.0–7.3 (2H, m), 7.6–8.1 (3H, m), 8.3–8.5 (1H, broad s).

EXAMPLE 6

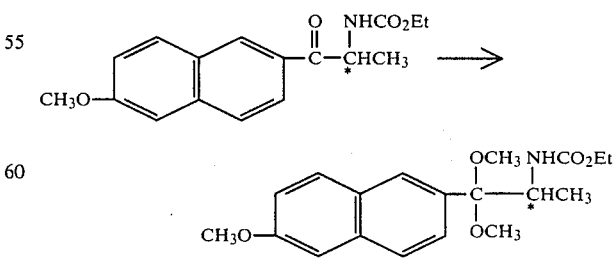

902 mg (3.00 mmols) of (+)-1-(6-methoxy-2-naphthyl)-2-(ethoxycarbonyl)amino-1-propanone and 6 ml of methyl orthoformate were stirred in 6 ml of anhydrous methanol at room temperature. 0.05 ml of methanesulfonic acid was added to the mixture which was then refluxed for 48 hours while stirring. The reaction mixture was cooled with ice and 20 ml of a saturated aqueous sodium bicarbonate solution was added in one portion. The mixture was extracted with methylene chloride (20 ml×2) and the extract was washed with water (20 ml×1), dried over anhydrous magnesium sulfate and concentrated under reduced pressure. The oily residue was purified by column chromatography [silica gel, ethyl acetate-hexane (1:2)] to obtain 781 mg of (+)-1-(6-methoxy-2-naphthyl)-2-(ethoxycarbonyl)amino-1-propanone dimethyl acetal as a colorless oily substance. Yield, 75%.

$[\alpha]_D^{21}$ −43.2° (c=1.277, chloroform).

IR (neat): 1733, 1515, 1277, 1220, 1178, 1055 cm$^{-1}$.

NMR (CDCl$_3$): δ1.04 (3H, d, J=6 Hz), 1.21 (3H, t, J=7 Hz), 3.24 (3H, s), 3.33 (3H, s), 3.88 (3H, s), 4.08 (2H, q, J=7 Hz), 4.1–4.6 (2H, m), 7.0–7.3 (2H, m), 7.47 (1H, dd, J=9 Hz and 2 Hz), 7.6–7.9 (3H, m).

EXAMPLE 7

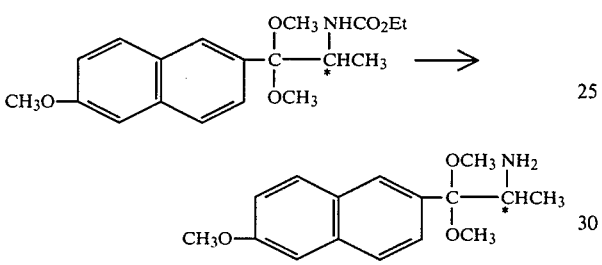

653 mg (1.8 mmols) of (−)-1-(6-methoxy-2-naphthyl)-2-(ethoxycarbonyl)amino-1-propanone dimethyl acetal and 5 ml of a 30% aqueous potassium hydroxide solution were heated at reflux in 50 ml of methanol for 5 days. After adding 20 ml of water, the mixture was extracted with ethyl acetate (20 ml×3), and the extract was dried over anhydrous magnesium sulfate and concentrated under reduced pressure. The residue was purified by column chromatography (Florisil, ethyl acetate) to obtain 300 mg of (+)-1-(6-methoxy-2-naphthyl)-2-amino-1-propanone dimethyl acetal as colorless crystals having a melting point of 84°–86° C. Yield, 58%.

$[\alpha]_D^{20}$ +3.44° (c=0.960, chloroform)

IR (KBr): 1610, 1488, 1173, 1119, 1047, 860 cm$^{-1}$.

NMR (CDCl$_3$): δ0.91 (3H, d, J=7 Hz), 1.14 (2H, s), 3.26 (3H, s), 3.28 (3H, s), 3.38 (1H, q, J=7 Hz), 3.87 (3H, s), 7.0–7.3 (2H, m), 7.49 (1H, dd, J=9 Hz and 2 Hz), 7.6–7.9 (3H, m).

EXAMPLE 8

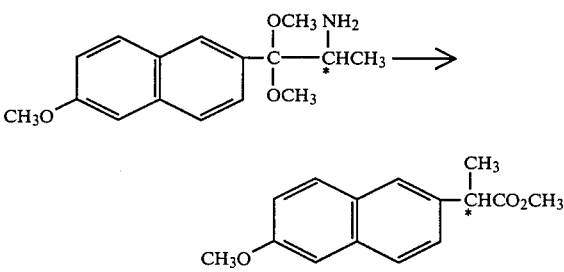

285 mg (1.04 mmol) of (+)-(6-methoxy-2-naphthyl)-2-amino-1-propanone dimethyl acetal was dissolved in 2 ml of acetic acid, followed by stirring at room temperature. 0.720 g (10.4 mmols) of sodium nitrite was then added thereto in small portions over a period of 3 hours and the mixture was stirred at that temperature for 17 hours. After adding 20 ml of water, the mixture was extracted with diethyl ether (15 ml×2), and the extract was washed with water (10 ml×3), dried over anhydrous magnesium sulfate and concentrated under reduced pressure. The residue was purified by column chromatography (silica gel, methylene chloride) to obtain 89 mg of methyl (+)-α-(6-methoxy-2-naphthyl)propionate. Yield, 35%.

$[\alpha]_D^{22}$ +20° (c=0.89, chloroform).

NMR (CDCl$_3$): δ1.54 (3H, d, J=7 Hz), 3.60 (3H, s), 3.79 (3H, s), 3.80 (1H, q, J=7 Hz), 7.0–7.8 (6H, m).

The product showed NMR spectrum substantially consistent with that of an authentic product of the dl pair.

EXAMPLE 9

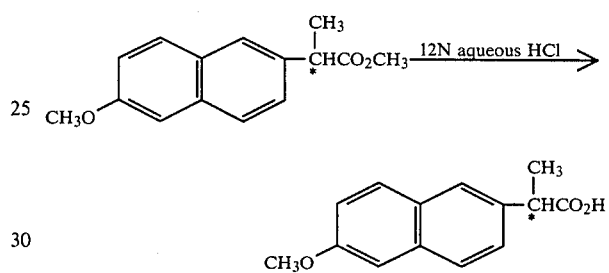

A mixture of 90 mg (0.37 mmol) of methyl (+)-α-(6-methoxy-2-naphthyl)propionate having a 100% optical purity [$[\alpha]_D^{20}$ +78.2° (CHCl$_3$)], 1 ml of 12N aqueous hydrochloric acid and 1 ml of dimethoxyethane was stirred at 50° C. for 23 hours. After adding 10 ml of water, the mixture was extracted with diethyl ether (8 ml×3), and the extract was washed with water (3 ml), dried over anhydrous magnesium sulfate and concentrated under reduced pressure. The resulting residue was purified by column chromatography [silica gel, hexane+ethyl acetate (1:2)] to obtain 49 mg of (+)-α-(6-methoxy-2-naphthyl)propionic acid as colorless crystals. Yield, 63%.

Melting Point: 155°–157° C.

$[\alpha]_D^{20}$ +67.2° (c=1.10, CHCl$_3$).

The product showed NMR spectrum substantially consistent with that of the corresponding racemic modification.

EXAMPLE 10

A mixture prepared by adding 23 g of d-2-(6-methoxy-2-naphthyl)propionic acid as prepared in Example 9 to 4 g of sodium hydroxide in 500 ml of aqueous methanol was stirred for 3 hours at room temperature. Then the mixture was evaporated to yield sodium d-2-(6-methoxy-2-naphthyl)propionate. THe product was replaced into toluene then isolated by centrifugation and washed with hexane prior to drying. The product melts at about 255° C. with decomposition and its infrared spectrum exhibits maxima at 1260, 1600, 1625 and 1725 cm$^{-1}$. The yield was 95% based on d-2-(6-methoxy-2-naphthyl)propionic acid.

What is claimed is:

1. A process for preparing an optically active 1-(6-methoxy-2-naphthyl)-2-(alkoxycarbonyl)amino-1- propanone derivatives and their halo analogs represented by the formula

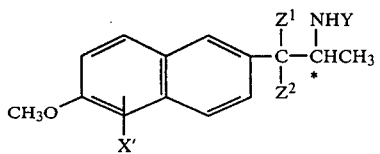

wherein X' is hydrogen or a halogen atom at 5 or 7 position of the naphthyl moiety; $Z_1$ and $Z_2$ together with its two bonds is an oxo group or $Z_1$ and $Z_2$ are $OR^1$ groups wherein $R^1$ represents a lower alkyl group or both $R^1$s may form, when taken together an alkylene group with 2 to 6 carbon atoms; Y is —COOR (wherein R is a lower alkyl group optionally substituted with one or more non-interfering substituents selected from hydroxy, alkoxy, acyloxy, nitro, alkylamino, halogen and carbonyl) or hydrogen; $Z_1$ and $Z_2$ are $OR^1$ groups when Y is hydrogen; the asterisk mark indicates an asymmetric carbon atom, which comprises:

(a) contacting an amide represented by the formula

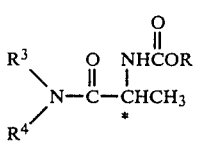

wherein R is as defined above; $R^3$ is a lower alkyl group; $R^4$ is a lower alkyl group or a lower alkoxy group, in an inert atmosphere and in an inert solvent comprising an ether, optionally first with a compound selected from the group consisting of alkyl lithium, aryl lithium, a Grignad r reagent, and alkali metal hydride, then with an organic metallic compound represented by the formula

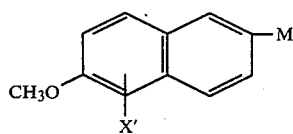

wherein X' is as defined above; M represents MgX wherein X is a halogen atom, or Li, to obtain optically active 1-(6-methoxy-2-naphthyl)-2-(alkoxycarbonyl)amino-1-propanone and its halo analogs represented by the formula .

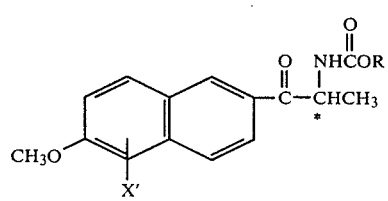

wherein X', R and the asterisk mark as defined above; and optionally (b) converting the compound of Formula (I) to a corresponding acetal represented by the formula:

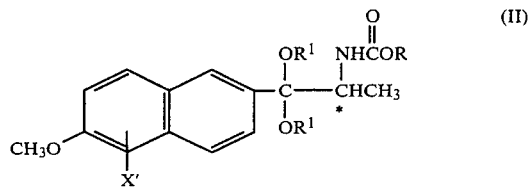

wherein X', R, $R^1$ and the asterisk mark are as defined above; and further optionally (c) contacting the compound of Formula (II) with a base to form the corresponding amino acetal represented by the formula

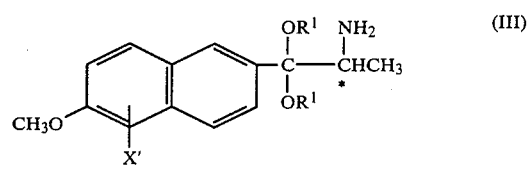

wherein X', $R^1$ and the asterisk mark are defined as above.

2. The process according to claim 1(a), wherein said alkyl lithium is n-, iso-, or t-butyl lithium, said aryl lithium is phenyl lithium, said Grignard reagent is methyl magnesium halide and said alkali metal hydride is sodium hydride respectively.

3. The process according to claim 1(a), wherein the reaction is carried out at a temperature of from $-100°$ C. to room temperature, preferably from $-78°$ C. to $0°$ C.

4. The process according to claim 1(a), wherein the reaction is conducted in nitrogen or argon.

5. The process according to claim 1(a), wherein the reaction is conducted in an ether or a mixture of an ether and another inert solvent.

6. The process according to claim 5, wherein said ether is diethyl ether, dioxane, 1,2-dimethoxyethane or tetrahydrofuran.

7. The process according to claim 5, wherein said other inert solvent is hexane, pentane, cyclohexane, benzene or toluene.

8. An optically active compound of the formula

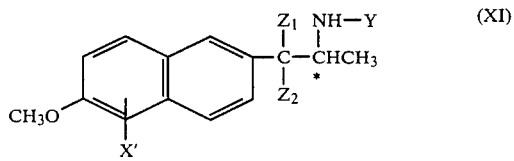

wherein X' is hydrogen or a halogen atom at 5 or 7 position of the naphthyl moiety, $Z_1$ and $Z_2$ together with its two bonds in an oxo group or $Z_1$ and $Z_2$ are $OR^1$ groups wherein $R^1$ represents a lower alkyl group or both $R^1$s may form, when taken together an alkylene group with 2 to 6 carbon atoms; Y is —COOR (wherein R is a lower alkyl group optionally substituted with one or more non-interfering substituents selected from hydroxy, alkoxy, acyloxy, nitro, alkylamino, halogen and carbonyl) or hydrogen; $Z_1$ and $Z_2$ are $OR^1$ groups when Y is hydrogen; the asterisk mark indicates an asymmetric carbon atom.

9. The compound according to claim 8 wherein X' is hydrogen; $Z_1$ and $Z^2$ together with its two bonds is an oxo group; Y is —COOR wherein R is a substituted or unsubstituted lower alkyl group.

10. A process for preparing optically active 2-(6-methoxy-2-naphthyl)propionic acid or its esters of the formula

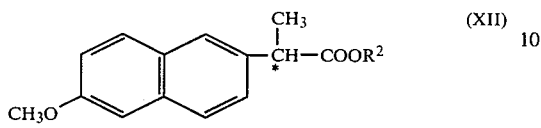

wherein $R^2$ is hydrogen, a lower alkyl group or a lower hydroxy alkyl group and asterisk mark indicates an asymmetric carbon atom, or a pharmaceutically acceptable salt thereof, which comprises:

(a) converting an optically active 1-(6-methoxy-2-naphthyl)-2-(alkoxycarbonyl)amino-1-propanone of the formula

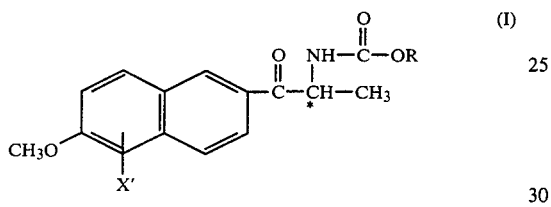

wherein X' is hydrogen or a halogen atom at 5 or 7 position of the naphthyl moiety; R is a lower alkyl group optionally substituted with one or more non-interfering substituents selected from hydroxy, alkoxy, acyloxy, nitro, alkylamino, halogen and carbonyl and the asterisk mark indicates an asymmetric carbon atom into its corresponding acetal and subsequently contacting said acetal so formed with a base to form a corresponding amino acetal of the formula

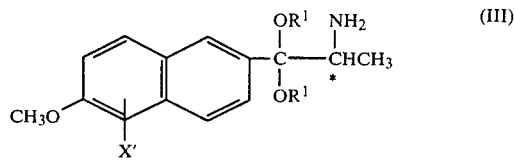

wherein X' is as defined above; $R^1$ is a lower alkyl group or two $R^1$ may form, when taken together, an alkylene group with 2 to 6 carbon atoms and optionally reacting the 5 or 7 halo compounds of Formula (III) with a reducing agent to remove the halogen atoms; and (b) contacting the amino acetal of Formula (III) with an N-nitrosolating agent in the presence of an aqueous solvent to form a compound of Formula

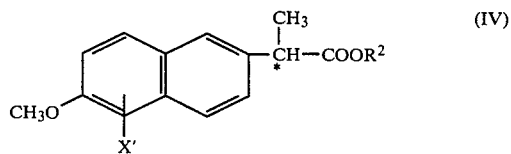

wherein X' and $R^2$ are as defined above; and if X' is halo, reacting the 5 or 7 halo compounds of Formula (IV) with a reducing agent to form the compound of Formula (XII); and optionally;

(c) converting a compound of Formula (XII) to its pharmaceutically acceptable salts.

* * * * *